(12) United States Patent
Zhao et al.

(10) Patent No.: US 10,783,655 B2
(45) Date of Patent: Sep. 22, 2020

(54) SYSTEM AND METHOD FOR ASSISTED PATIENT POSITIONING

(71) Applicant: Siemens Healthcare GmbH, Erlangen (DE)

(72) Inventors: Zhuokai Zhao, Baltimore, MD (US); Yao-jen Chang, Princeton, NJ (US); Ruhan Sa, Amherst, NY (US); Kai Ma, Princeton, NJ (US); Jianping Wang, Plainsboro, NJ (US); Vivek Kumar Singh, Princeton, NJ (US); Terrence Chen, Princeton, NJ (US); Andreas Wimmer, Forchheim (DE); Birgi Tamersoy, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 230 days.

(21) Appl. No.: 15/950,435

(22) Filed: Apr. 11, 2018

(65) Prior Publication Data
US 2019/0318497 A1 Oct. 17, 2019

(51) Int. Cl.
*G06K 9/00* (2006.01)
*G06T 7/70* (2017.01)
*G06T 7/285* (2017.01)
*G06T 7/593* (2017.01)

(52) U.S. Cl.
CPC ............... *G06T 7/70* (2017.01); *G06T 7/285* (2017.01); *G06T 7/593* (2017.01); *G06T 2207/10012* (2013.01); *G06T 2207/10072* (2013.01); *G06T 2207/20084* (2013.01); *G06T 2207/20221* (2013.01); *G06T 2207/30196* (2013.01); *G06T 2210/41* (2013.01)

(58) Field of Classification Search
CPC ........... G06T 7/70; G06T 7/285; G06T 7/593; G06T 2207/10012; G06T 2207/10072; G06T 2207/20084; G06T 2207/20221; G06T 2207/30196; G06T 2210/41
See application file for complete search history.

(56) References Cited

U.S. PATENT DOCUMENTS

| | | | | |
|---|---|---|---|---|
| 6,049,281 A * | 4/2000 | Osterweil | ............ | A61B 5/1128 340/573.1 |
| 8,834,372 B2 * | 9/2014 | Lundberg | ............ | G01S 7/52085 600/443 |
| 9,668,699 B2 * | 6/2017 | Georgescu | ............ | A61B 5/7267 |
| 2002/0065461 A1 * | 5/2002 | Cosman | ............... | A61B 6/5247 600/426 |
| 2017/0352131 A1 * | 12/2017 | Berlin | ................. | H04N 5/23222 |

(Continued)

OTHER PUBLICATIONS

Snavely, N. et al., "Photo Tourism: Exploring image collections in 3D" ACM Transactions on Graphics, 2006, 12 pgs.

(Continued)

*Primary Examiner* — Shefali D Goradia

(57) ABSTRACT

A method of obtaining a medical image includes obtaining, via a camera, at least one surface image of a patient. A pose of the patient is determined from the at least one surface image of the patient using at least one spatial information module. The patient is positioned, via a moveable bed, to an imaging start position and a medical image of the patient is obtained using a medical imaging modality.

19 Claims, 15 Drawing Sheets

(56) References Cited

U.S. PATENT DOCUMENTS

2018/0289310 A1* 10/2018 Girouard .............. A61B 5/4094
2019/0080442 A1* 3/2019 Berlin ................. A61N 5/1048

OTHER PUBLICATIONS

Leonard, John J., et al., "Simultaneous Map Building and Localization for an Autonomous Mobile Robot" IEEE/RSJ International Workshop on Intelligent Robots and Systems, IROS 1991, Nov. 3-5, 1991, Osaka, Japan, IEEE Cat. No. 91TH0375-6.

Mur-Artal, Raul, et al., "ORB-SLAM: A Versatile and Accurate Monocular Slam System" IEEE Transactions on Robotics, vol. 31, No. 5, Oct. 2015, pp. 1147-1163.

Fuhrmann, Simon, et al., "MVE: A Multi-View Reconstruction Environment" Proceedings of the Eurographics Workshop on Graphics and Cultural Heritage, Darmstadt, Germany, 2014.

Chang, Yao-Jen, and Chen, Tsuhan "Image-based Rendering" Book Chapter in Academic Press Library in Signal Processing, vol. 4: Image, Video Processing and Analysis, Hardware, Audio, Acoustic and Speech Processing, Academic Press, 2013.

Peng, Xi, et al. "A Recurrent Encoder-Decoder Network for Sequential Face Alignment" European Conference on Computer Vision, pp. 38-56, Springer International Publishing, 2016.

Li, Ke, et al.. "Iterative Instance Segmentation" Proceedings of the IEEE Conference on Computer Vision and Pattern Recognition, pp. 3659-3667, 2016.

Newell, Alejandro, et al. "Stacked Hourglass Networks for Human Pose Estimation" European Conference on Computer Vision, pp. 483-499, Springer International Publishing, 2016.

Shi, X. et al., "Convolutional LSTM Network: A Machine Learning Approach for Precipitation Nowcasting" Advances in geural Information Processing Systems 28 (NIPS 2015), pp. 802-810.

Krizhevsky, Alex, et al. "ImageNet Classification with Deep Convolutional Neural Networks" Advances in Neural nformation Processing Systems, pp. 1097-1105, 2012.

Simonyan, Karen, and Zisserman, Andrew "Very Deep Convolutional Networks for Large-Scale Image Recognition" https://arxiv.org/abs/1409.1556v6 (2014).

He, Kaiming, et al. "Deep Residual Learning for Image Recognition" Proceedings of the IEEE Conference on Computer Vision and Pattern Recognition, pp. 770-778, 2016.

Chen, Xianjie, and Yuille, Alan L. "Articulated Pose Estimation by a Graphical Model with Image Dependent Pairwise Relations" Advances in Neural Information Processing Systems, pp. 1736-1744, 2014.

Huang, Gao, et al. "Densely Connected Convolutional Networks" Proceedings of the IEEE Conference on Computer Vision and Pattern Recognition, pp. 4700-4708, 2017.

Tompson, J. et al., "Join Training of a Convolutional Network and a Graphical Model for Human Pose Estimation" NIPS, pp. 1-9, 2014.

Tompson, J. et al., "Efficient Object Localization Using Convolutional Networks" Proceedings of the IEEE Conference on Computer Vision and Pattern Recognition, pp. 648- 656, 2015.

Cao, Zhe, et al., "Realtime Multi-Person 2D pose estimation using Part Affinity Fields" Proceedings of the IEEE Conference on Computer Vision and Pattern Recognition, 2017, pp. 7291-7299, https://arxiv.org/abs/1611.08050.

Chu, X. et al."Multi-Context Attention for Human Pose Estimation" Proceedings of the IEEE Conference on Computer Vision and Pattern Recognition, pp. 1831-1840, 2017.

Bulat, A. and Tzimiropoulos, G. "Human Pose Estimation via Convolutional Part Heatmap Regression" https://arxiv.org/abs/1609.01743 (2016).

Pishchulin, L. et al., "DeepCut: Joint Subset Partition and Labeling for Multi Person Pose Estimation" Proceedings of the IEEE Conference on Computer Vision and Pattern Recognition, pp. 4929-4937, 2016.

Insafutdinov, E. et al., "DeeperCut: A Deeper, Stronger, and Faster Multi-Person Pose Estimation Model" https://arxiv.org/abs/1605.03170 (2016).

Wei, Shih-En et al., "Convolutional Pose Machines" Proceedings of the IEEE Conference on Computer Vision and Pattern Recognition, pp. 4724-4732, 2016.

Charles, J. et al., "Personalizing Human Video Pose Estimation" Proceedings of the IEEE Conference on Computer Vision and Pattern Recognition, pp. 3063-3072, 2016.

Song, J. et al., "Thin-Slicing Network: A Deep Structured Model for Pose Estimation in Videos" Proceedings of the IEEE conference on computer vision and pattern recognition, pp. 4220-4229, 2017.

Mehta, D. et al., "VNect: Real-time 3D Human Pose Estimation with a Single RGB Camera" ACM Transactions on Graphics, vol. 36, No. 4, Article 44, Jul. 2017.

Lin, M. et al., "Recurrent 3D Pose Sequence Machines" Proceedings of the IEEE Conference on Computer Vision and Pattern Recognition, pp. 810-819, 2017.

Li, Fu et al., "Temporal Modeling Approaches for Large-scale Youtube-8M Video Understanding" https://arxiv.org/abs/1707.04555, CVPR 2017 YouTube-8M Workshop.

* cited by examiner

370

380

SYSTEM AND METHOD FOR ASSISTED PATIENT POSITIONING

FIELD

Aspects of the present disclosure relate in general to patient monitoring during medical imaging, and more particularly to patient positioning during medical imaging.

BACKGROUND

Ensuring proper patient positioning, identifying, and/or correcting for movement are key elements of medical imaging, such as computed-tomography scans (CT scans), positron emission tomography (PET) scans, magnetic resonance imaging (MRI), and/or other medical imaging. In some instances, cameras may be mounted to a medical imaging device to provide position and movement data of a patient during a medical imaging scan. However, cameras mounted to the medical imaging device provide limited field of view, which limits the use of such images in image analytics during scans.

In addition, current systems require an operator to perform one or more adjustments to a moveable bed to properly position a patient prior to initiating a medical imaging scan. Improper positioning leads to errors or artifacts in the medical image. However, operator adjustments can be time consuming and require operators to spend time away from other tasks, such as scan monitoring, patient preparation, etc. to perform such adjustments.

SUMMARY

In various embodiments, a method for generating a medical image is disclosed. The method includes the step of obtaining, via a camera, at least one surface image of a patient. The pose of the patient is determined from the at least one surface image using at least one spatial information module. The patient is positioned, via a moveable bed, at an imaging start position and a medical image of the patient is obtained using a medical imaging modality.

In various embodiments, a system of generating a medical image is disclosed. The system includes an imaging modality configured to obtain a medical image of a patient, an imaging device configured to obtain at least one surface image of a patient, and a processor configured to implement at least one of a spatial information module, a temporal information module, or a combination thereof. The processor is configured to receive the at least one surface image of the patient and verify at least one of a patient pose or a body region. The processor is further configured to execute a medical imaging procedure using the imaging modality when the patient pose or body region is verified.

In various embodiments, a non-transitory computer-readable medium encoded with computer executable instructions is disclosed. The computer executable instructions, when executed by a computer in a system for obtaining a medical image, cause the system for obtaining a medical image to execute the step of receiving at least one surface image of a patient and determining a pose of the patient from the at least one surface image using at least one spatial information module. The patient is positioned, via a moveable bed, at an imaging start position and a medical image of the patient is obtained via a medical imaging modality.

BRIEF DESCRIPTION OF THE DRAWINGS

The following will be apparent from elements of the figures, which are provided for illustrative purposes and are not necessarily drawn to scale.

DETAILED DESCRIPTION

This description of the exemplary embodiments is intended to be read in connection with the accompanying drawings, which are to be considered part of the entire written description.

Various embodiments of the present disclosure address the foregoing challenges associated with patient positioning and monitoring in medical imaging, such as computed-tomography (CT), for example, by using a one or more two-dimensional (2D) images obtained by a camera mounted to an outer surface of an imaging device to position a patient prior to initiating a medical imaging procedure and to monitor the patient for movement during the procedure.

Figure 1:
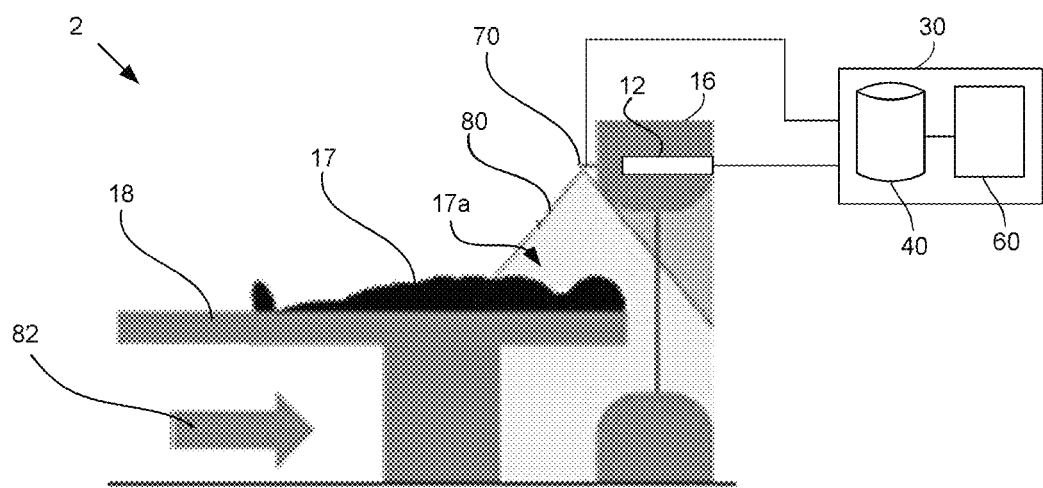
FIG. 1 illustrates a medical imaging system including an imaging device coupled to an outer surface of a gantry and having a limited field of view, in accordance with some embodiments.

FIG. 1 illustrates one embodiment of a medical imaging system 2. The medical imaging system 2 includes a scanner for at least a first medical imaging modality 12 provided in a first gantry 16. The first modality 12 includes a plurality of detectors configured to detect an annihilation photon, gamma ray, and/or other medical imaging event. In various embodiments, the first modality 12 is a CT detector, a positron-emission tomography (PET) detector, single-photon emission tomography (SPECT) detector, and/or any other suitable detector. A patient 17 lies on a movable patient bed 18 that may be movable with respect to one or more gantries 16. In some embodiments, the medical imaging system 2 includes a scanner for a second medical imaging modality provided in a second gantry. The second medical imaging modality can be any suitable imaging modality, such as, for example, PET, single-photon emission tomography (SPECT), CT and/or any other suitable imaging modality.

In some embodiments, an imaging device 70 is mounted to an exterior surface of the medical imaging system 2, such as a housing of the medical imaging system 2, the housing of one or more gantries 16, and/or any other suitable surface. The imaging device 70 can include a two-dimensional (2D) imaging device, such as, for example, a digital camera (such as a charge-coupled device (CCD), a complementary metal-oxide semiconductor (CMOS) device, and/or any other suitable device). The imaging device 70 is configured to generate one or more images of a portion 17*a* of a patient 17 positioned outside of the gantry 16. In some embodiments, the imaging device 70 includes a limited field of view capable of imaging a sub-portion of the patient 17 positioned outside of the imaging modality 12. The imaging device 70 can be configured to provide continuous (i.e., video) and/or discrete images of the patient 17.

Scan data from the first modality 12 (and/or the second modality if included) is stored at one or more computer databases 40 and processed by one or more computer processors 60 of a computer 30. In some embodiments, image data from the imaging device 70 may also be stored and/or processed by the computer 30, for example, stored in the databases 40 and/or processed by a processor 60. The graphical depiction of computer 30 in FIG. 1 is provided by way of illustration only, and computer 30 may include one or more separate computing devices. The imaging data sets can be provided directly by the first modality 12, the second modality, and/or the imaging device 70 to the computer 30 and/or may be provided as a separate data set, such as, for example, from a memory coupled to the computer 30. The computer 30 can include one or more processing electronics for processing a signal received from one of the plurality of imaging modalities 12 and/or the imaging device 70. In some embodiments, and as described in greater detail below, the processor 60 is configured to execute one or more computer executable instructions and perform one or more steps for identifying a patient pose, positioning a patient at a start position, and generating at least one medical image.

Figure 2:
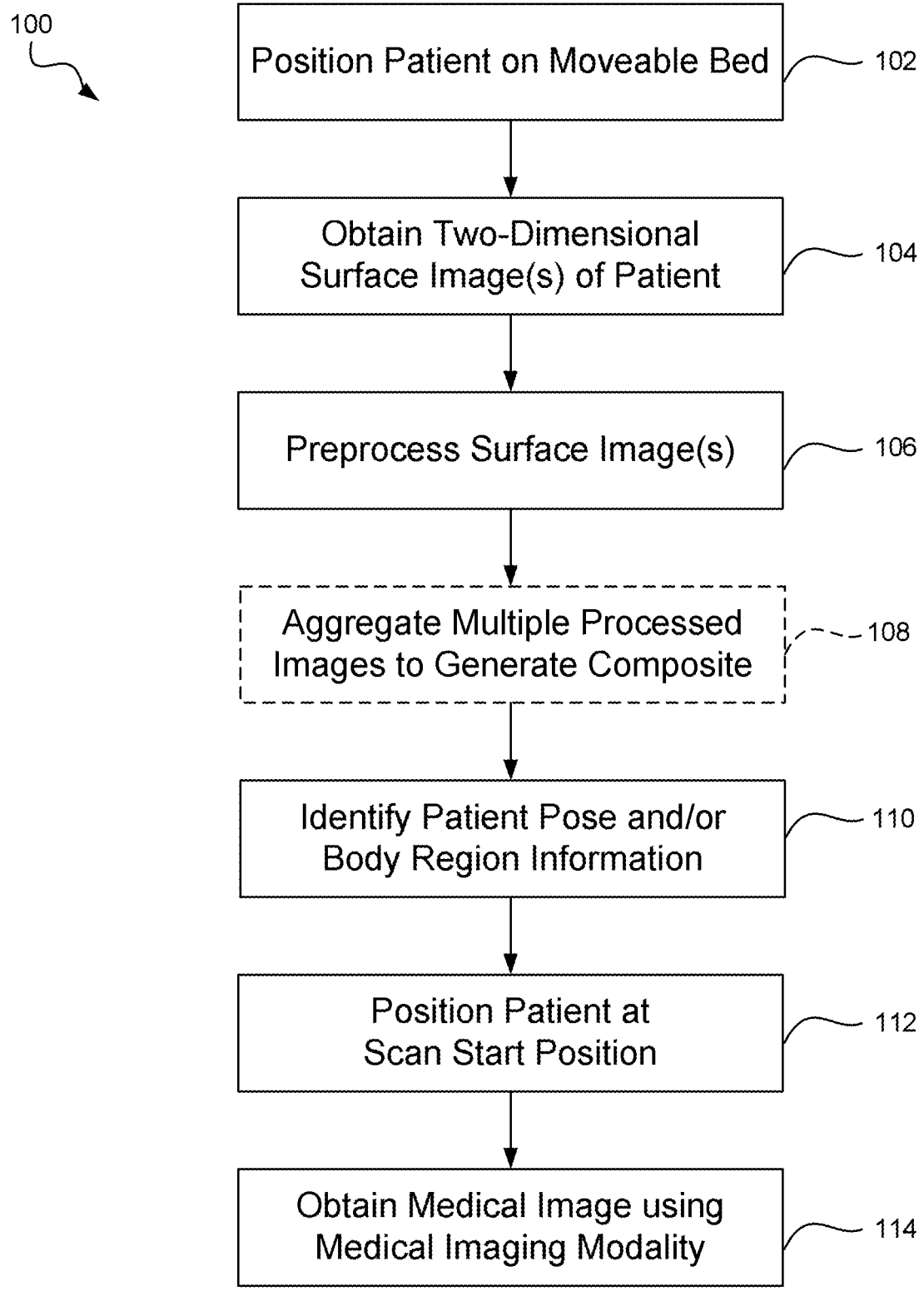
FIG. 2 illustrates a method of identifying a body pose of a patient and positioning a patient at a start position, in accordance with some embodiments.
Figure 3:
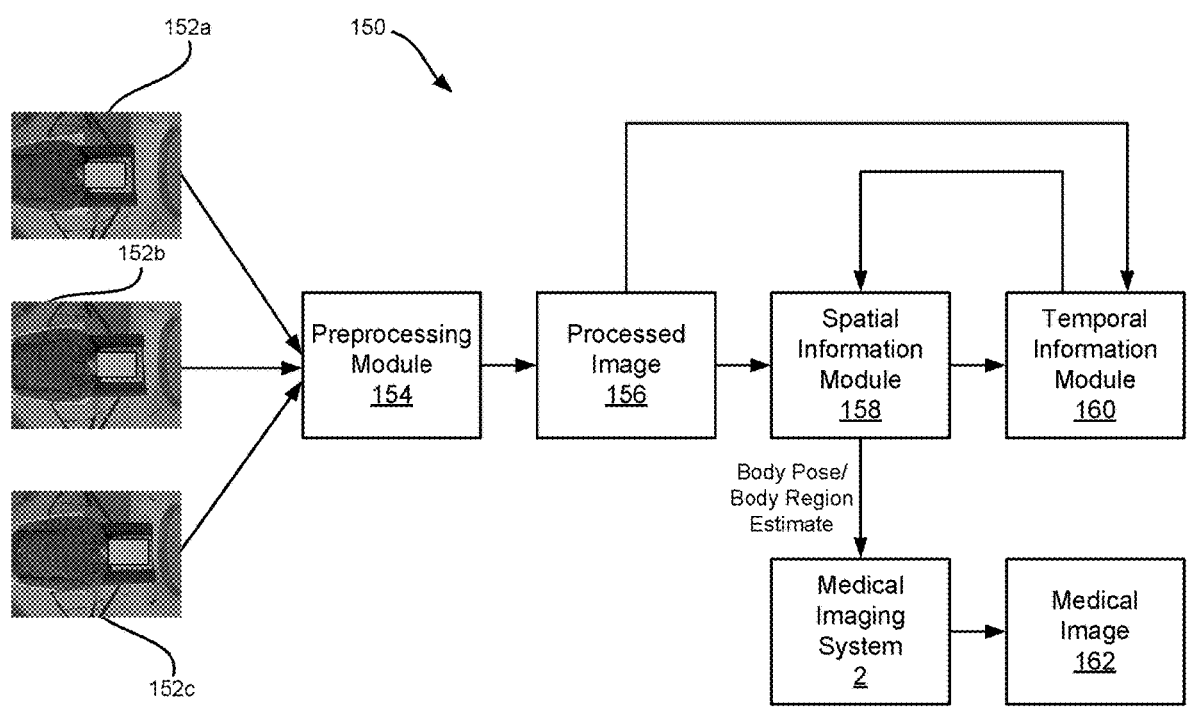
FIG. 3 illustrates a process flow of the method of FIG. 2, in accordance with some embodiments.

FIG. 2 illustrates a method 100 of identifying a body pose of a patient 17 and positioning a patient 17 at a start position, in accordance with some embodiments. FIG. 3 illustrates a process flow 150 of the method 100 of FIG. 2, in accordance with some embodiments. At step 102, a patient 17 is positioned on a patient bed 18 that is moveable with respect to at least one gantry 16 containing at least one medical imaging modality 12. The patient 17 can be positioned on the bed in one or more poses (or combinations of poses), such as feet-first, head-first, supine, prone, etc. In some embodiments, the pose of the patient 17 relates to an imaging procedure to be performed. For example, in some embodiments, the patient 17 may be posed advantageously for a selected imaging procedure, such as being positioned in a head-first, supine pose, head-first prone pose, feet-first supine pose, or a feet-first prone pose. Although specific poses are discussed herein, it will be appreciated that the patient 17 can be positioned on the patient bed 18 in any suitable pose.

At step 104, one or more surface images 152*a*-152*c* of the patient 17 are obtained using an imaging device 70 coupled to an outer surface of the medical imaging system 2. The images 152*a*-152*c* can be discrete images and/or continuous images (i.e., video) obtained by the imaging device 70. In some embodiments, the one or more images 152*a*-152*c* have a limited field-of-view such that only a portion 17*a* of the patient 17 is visible in each image obtained by the imaging device 70. For example, imaging of the patient 17 may be limited to one or more body regions such as, for example, head, thorax, abdomen, pelvis, legs, etc. The images 152*a*-152*c* obtained by the imaging device 70 may be further impacted by one or more occlusions (such as hospital gowns and/or other coverings), affected by lighting conditions, and/or impacted by artifacts and/or distortions. In some embodiments, the imaging device includes a 2D imaging device, such as a 2D red-green-blue (RGB) imaging device or a monochrome imaging device configured to obtain discrete and/or continuous images of a patient 17.

At step 106, the one or more images are provided to a preprocessing module 154 configured perform one or more corrections and/or otherwise preprocess an image 152*a*-152*c* captured by the imaging device 70. For example, the preprocessing module 154 can be configured to remove artifacts, correct distortions, and/or provide any other suitable correction. In some embodiments, the preprocessing module 154 can be configured to apply image filtering (e.g., low-pass filtering, high-pass filtering, bilateral filtering, Fourier filtering, etc.), linear transformations (e.g., identity, reflection, scaling, rotation, shear, etc.), non-linear transformations (e.g., un-distortion based on lens distortion parameters obtained from camera calibration), and/or any other suitable image preprocessing. The preprocessing module 154 generates a processed image 156 for each image 152*a*-152*c* obtained by the imaging device 70.

At optional step 108, each of the processed images 156 is provided to a temporal information module 160 configured to aggregate information from multiple processed images 156 to generate a stitched image and/or improve patient body region estimates through temporal network learning. The temporal information module 160 can include one or more individual networks and/or modules configured to analyze multiple processed images 156 simultaneously and/or sequentially to generate an aggregate image. The temporal information module 160 can be configured to apply a multi-frame analytics process to improve body region estimates, configured to combine multiple processed images 156 to generate an aggregate image having a greater field-of-view than any single processed image 156, and/or configured to perform additional or alternative image aggregation procedures. The temporal information module 160 can include one or more neural networks, as discussed in greater detail below.

At step 110, each processed images 156 is provided to a spatial information module 158 configured to identify a patient pose (e.g., head-first/feet-first, supine/prone, etc.) and/or identify specific patient regions contained within the processed image 156 (e.g., head, thorax, abdomen, lower body, etc.). The spatial information module 158 can include one or more individual networks and/or modules configured to analyze an image 156 to identify a specific patient pose and/or body region. In some embodiments, the spatial information module 158 is configured to apply a single-frame analytics process to identify a patient pose and/or body region, such as one or more a neural networks, as discussed in greater detail below. Although steps 106-110 are illustrated as distinct steps, it will be appreciated that preprocessing, spatial information analysis, and/or temporal information analysis can be performed by a single network and combined into a single step in some embodiments.

At step 112, the patient 17 is positioned at a start position that is optimized and/or ideal for one or more medical imaging scans to be performed. For example, in some embodiments, the patient bed 18 is moved to position a portion 17a of a patient 17 to be scanned within a field-of-view of a medical imaging modality 12, at a start position associated with the medical imaging modality 12, and/or in any other advantageous position. The medical imaging system 2 can position the patient 17 using movement devices formed integrally with the medical imaging system 2, such as one or more motors operatively coupled to the patient bed 18. The ideal starting position of the patient 17 is related to the imagine procedure to be performed and the patient 17 is positioned in the ideal starting position automatically (e.g., without user interaction) prior to initiating a medical imaging scan. The positioning can be performed automatically by the medical imaging system 2 based on the patient pose and/or body region identification performed by the computer 30.

In some embodiments, the medical imaging system 2 is configured to use the generated body pose and/or body region estimates to verify proper pose of a patient, position a patient 17 at a start position, and/or automatically initiate a medical imaging procedure. For example, in some embodiments, the medical imaging system 2, such as the computer 30, is configured to compare a body pose estimate generated by the spatial information module 158 to a predetermined pose that is required for and/or optimal for one or more selected medical imaging procedures. If the pose estimate matches the predetermined pose, the medical imaging system 2 generates an indication that the patient pose is proper for the selected imaging procedure. If the pose estimate does not match the predetermined pose, the medical imaging system 2 can generate an indication, either to an operator and/or a patient, to correct the patient pose prior to initiating the medical imaging procedure.

In some embodiments, the medical imaging system 2 is configured to position a patient 17 at a predetermined start position corresponding to a selected and/or ideal start position for one or more predetermined medical imaging procedures. For example, in some embodiments, a medical imaging procedure may correspond to imaging of one or more body regions, such as a head, thorax, abdomen, pelvis, legs, etc. The medical imaging system 2 is configured to identify one or more body regions from a plurality of images obtained by the imaging device 70 and position the patient 17 such that a selected body region is positioned at an ideal starting position for a medical imaging procedure, such as being positioned at a start of a field-of-view for a first imaging modality 12. The medical imaging system 2 can determine the position of the selected body region directly (e.g., body region visible in one or more images and positioned relative to gantry 16) and/or indirectly (e.g., body region not visible but can be calculated by additional body regions visible in one or more images). In some embodiments, the patient 17 can be generally positioned by an operator and the medical imaging system 2 can perform minor and/or additional positioning prior to starting the medical imaging procedure.

At step 114, a medical image 162 is obtained using one or more of the medical imaging modalities 12 formed integrally with the medical imaging system 2. The medical image 162 can be obtained according to any predetermined imaging process, such as, for example, continuous-bed motion (CBM) imaging (e.g., CBM CT, CBM PET, etc.), step-and-shoot imaging, and/or fixed location imaging. The medical image 162 can be processed according to any known method to generate a medical image of the predetermined portion of the patient. In some embodiments, the medical imaging system 2 is configured to automatically initiate a medical imaging procedure after positioning the patient 17 at a start position.

Figure 4:
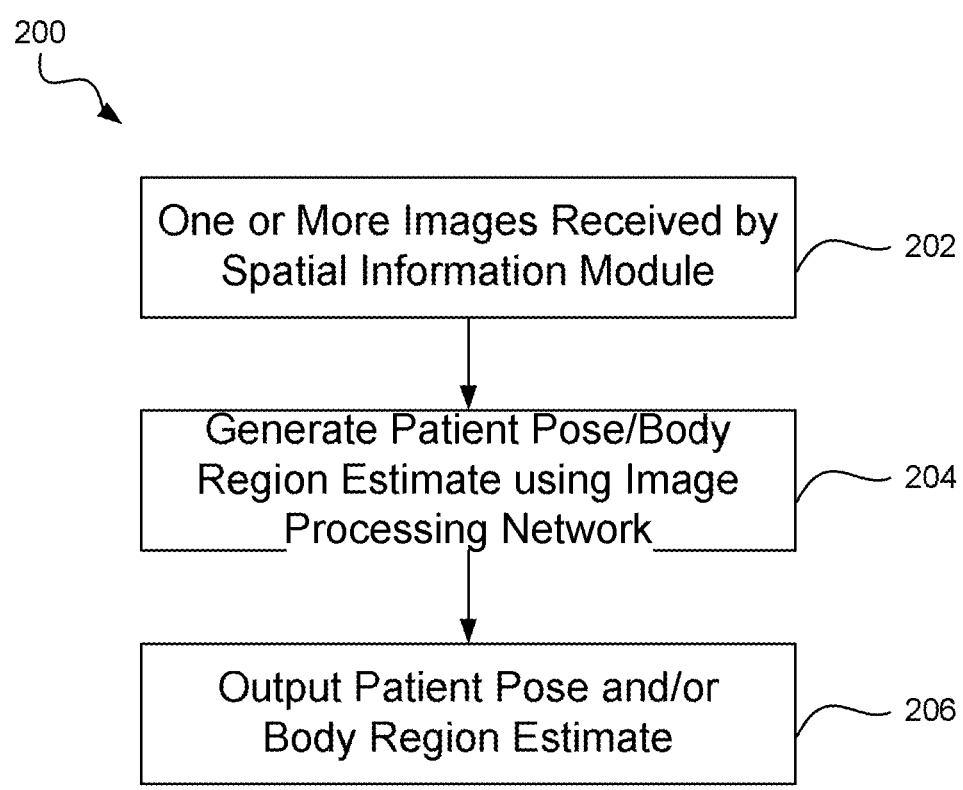
FIG. 4 illustrates a method of single-frame analytics configured to identify a patient pose and/or body region boundary, in accordance with some embodiments.
Figure 5:
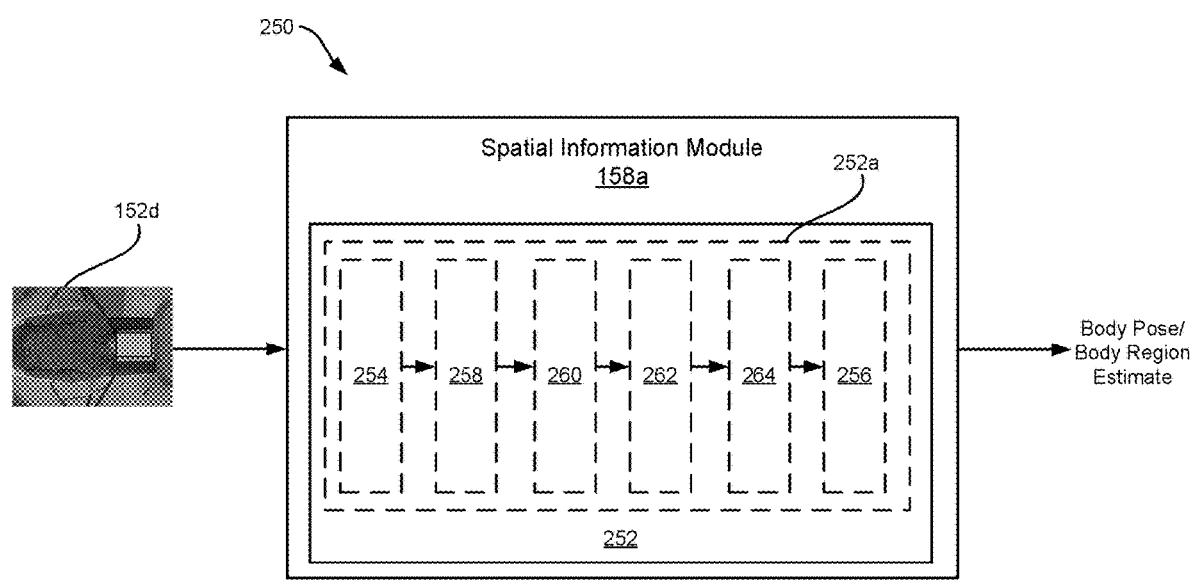
FIG. 5 illustrates a process flow of a spatial information module configured to implement the method illustrated in FIG. 4, in accordance with some embodiments.

FIG. 4 illustrates a method 200 of single-frame analytics configured to identify a patient pose and/or body region boundaries, in accordance with some embodiments. FIG. 5 illustrates a process flow 250 of a spatial information module 158a configured to implement the method 200 illustrated in FIG. 4, in accordance with some embodiments. At step 202, at least one image 152d is received by the spatial information module 158a. In some embodiments, the spatial information module 158a includes a single-frame analytics network configured to process each image 152d (i.e., frame) obtained by the imaging device 70.

At step 204, each image 152d is provided to an image processing network 252 and, at step 206, the image processing network 252 outputs a patient pose and/or body region estimate. The image processing network 252 can include at least neural network configured to identify a patient pose and/or body region in each image 152d. For example, in some embodiments, the image processing network 252 includes a fully convolutional neural network (FCNN) 252a. The FCNN 252a includes a plurality of layers, such as one or more input layers 254, one or more output layers 256, and/or one or more hidden layers 258-264. Each of the hidden layers can include one or more of a convolutional layer, a pooling layer, a fully connected layer, and/or a normalization layer.

In some embodiments, each of the convolutional layers 258 applies a convolution operation and/or a cross-correlation operation to an input. The output of the convolution layer 258 is provided to a subsequent layer, such as a pooling layer 260. The convolutional layer 258 has a plurality of parameters including a set of learnable filters (referred to as kernels) which have a small receptive field (i.e., small field-of-view) that extends through the full depth of the input volume. The input volume can be convoluted across a width and/or a height to generate an output, such as a dot product output, between the entries of the filter and the input. The convolution generates a 2D activation map. In some embodiments, the convolution layer 258 stacks activation maps for all filters along the depth dimension to form a full output volume of the convolution layer 258. Each entry in an output can be interpreted as an output of small region (i.e., neuron) in an input and shares parameters with neurons in the activation map. In some embodiments, the FCNN 252a can include a parameter sharing scheme configured to control the number of free parameters in each convolutional layer. The FCNN 252a can denote 2D slices within the depth dimension of the image and use the same weights and/or biases for each neuron within the slice.

In some embodiments, the FCNN 252a includes at least one pooling layer 260 configured to perform non-linear down-sampling. Each pooling layer 260 can include one or more non-linear functions, such as, for example, a max pooling function, an average pooling function, an L2-norm pooling function, and/or any other suitable pooling function. For example, in embodiments including max pooling, each pooling layer is configured to partition an input image into a set of non-overlapping rectangles and maximize an output for each non-overlapping rectangle. Pooling layers 260 may be configured to progressively reduce the spatial size of the representation, to reduce the number of parameters and amount of computing in the network, and/or to control overfitting. In some embodiments, a pooling layer 260 is configured to operate independently on each slice of the input, for example, performing spatial resizing.

In some embodiments, the FCNN 252a includes one or more fully connected layers 262. The fully connected layers 262 are configured to provide connections to all activated neurons in a previous layer 258, 260. The activations can be computed with a matrix multiplication and/or a bias offset to provide additional input to subsequent convolution layers. In various embodiments, one or more FCNN networks may be implemented, for example, modified version of AlexNet, VGG CNN, ResNet, and/or any other suitable CNN network.

Figure 6:
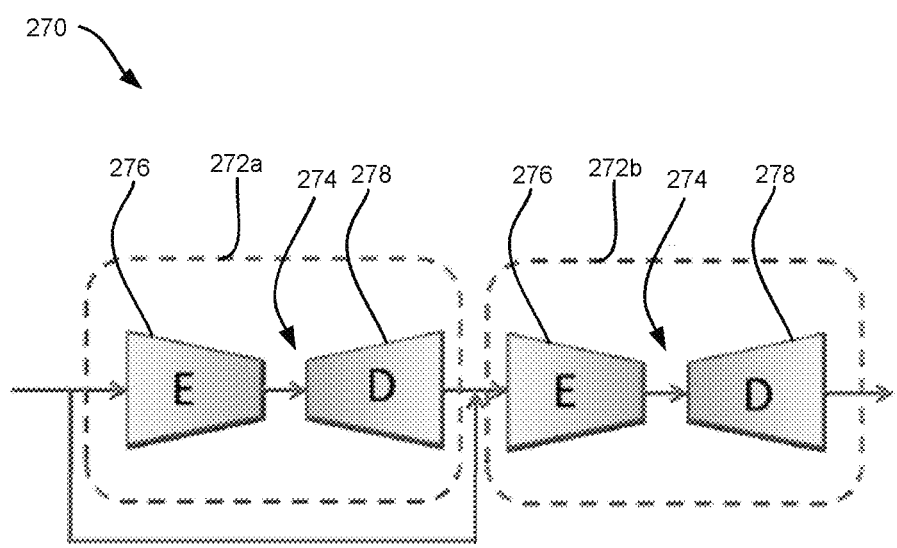
FIG. 6 illustrates a stacked encoder-decoder network including a Dense Block Hourglass (DBHG) network, in accordance with some embodiments.

In some embodiments, the FCNN 252a includes a stacked fully convolutional encoder-decoder network 270, as illustrated in FIG. 6, which is configured to progressively refine a prediction of a patient pose and/or body region by aggregating the intermediate results and features across different scales. The stacked fully convolutional encoder-decoder network 270 is a spatial recurrent network that receives a prediction from a previous iteration (or stage) 272a as an input to each subsequent stage 272b to progressively refine the prediction via information aggregation and error feedback mechanisms.

Figure 7:
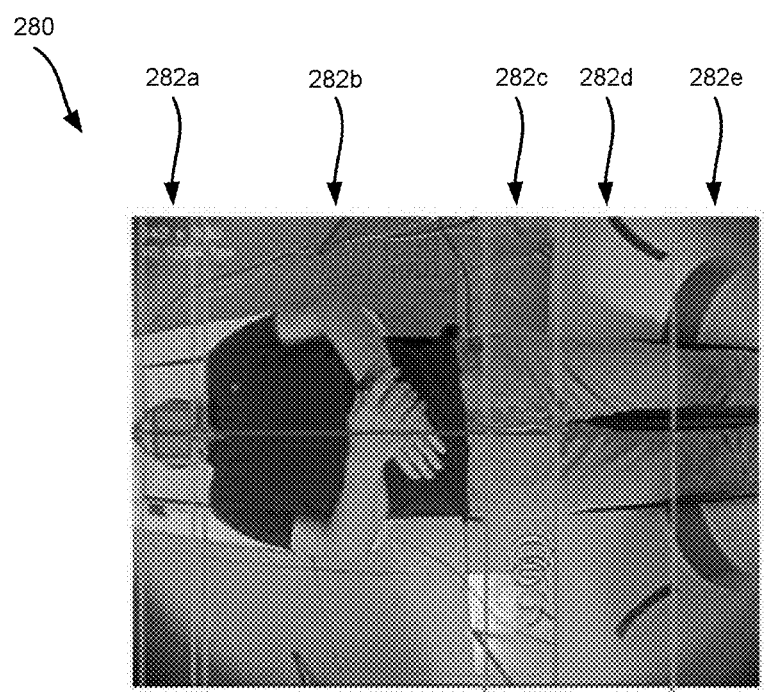
FIG. 7 illustrates an image of a patient having a plurality of segments corresponding to identified body regions, in accordance with some embodiments.

In some embodiments, the FCNN 252a is configured to enforce structural inference by spatial modeling of one or more body regions. As illustrated in FIG. 7, in some embodiments, the FCNN 252a segments a patient body 17 into a plurality of regions 282a-282e, for example, to generate a tree structure 280. The tree structure can be characterized by the following equation, wherein in some embodiments, I denotes an input image 152a and x denotes the location of L body region boundaries (where $x=\{x_1, x_2, \ldots, x_L\}$. The conditional probability $p\{x|I,\Theta)$ parametrized by $\Theta$ can be modeled as:

$$p(x | I, \theta) = \frac{\exp[-E(x, I, \theta)]}{z},$$

where Z is the normalization factor, defined as $Z=\Sigma_{x \in x} \exp\{-E(x,I,\theta)\}$. Based on the tree structure 280 of the patient 17, an undirected graph $G=(v,\varepsilon)$, where v specifies the positions of the body region boundaries, and $\varepsilon$ denotes sets of edges connecting body regions. Furthermore, the energy function can be expressed as follows:

$$E(x,I,\theta)=\Sigma_{i \in v}\psi_u(x_i)+\Sigma_{(i,j) \in \varepsilon}\psi_p(x_i,x_j),$$

where the unary energy component $\psi_u(x_i)$ measures the inverse likelihood of the position of the $i^{th}$ body region boundary at $x_i$, and the pairwise energy component $\psi(x_i,x_j)$ measures the correlation between body regions configuration $x_i$ and $x_j$. In some embodiments, the unary energy component is determined (e.g., predicted) by the FCNN 252a, for example as a heatmap for each body region 282a-282e, and the pairwise energy term may be characterized by a spring model, although it will be appreciated that other approaches for estimating and/or determining the unary and/or pairwise energy terms may be used.

In some embodiments, a single network can be configured to jointly estimate the pose and body region of a patient. For example, in some embodiments, the neural network 252 includes a multi-task learning framework configured to share features in one or more layers for different supervision signals. The neural network 252 can use shared features to jointly estimate a pose and/or a body region of a patient 17 within an image 152a-152c.

Figure 8:
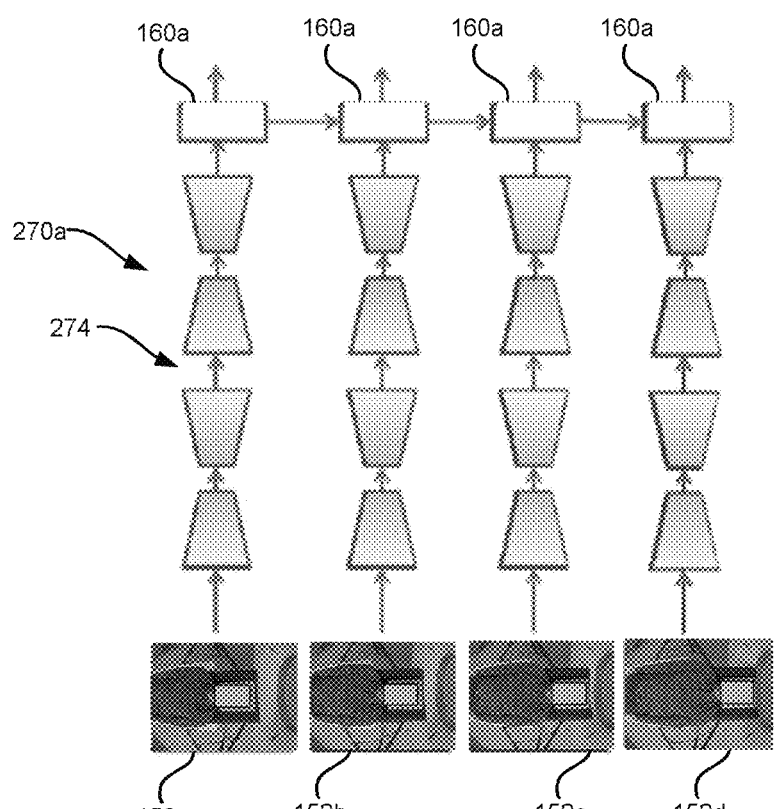
FIG. 8 illustrates a recurrent neural network (RNN) configured to capture temporal information integrated into a stacked encoder-decoder network, in accordance with some embodiments.

With reference again to FIG. 6, in some embodiments, a stacked encoder-decoder network 270 includes a Dense Block Hourglass (DBHG) network 270. Each DBHG 270 includes a plurality of stages 272a, 272b each having at least one hourglass 274 generated as a Dense Block (or other suitable network) including an encoder portion 276 and a decoder portion 278. For example, in some embodiments, the stacked encoder-decoder network 270 includes a stacked 2 DBHG, with each hourglass 274 having a predetermined depth (for example, a depth of four), and each dense block having four bottleneck connections (as illustrated in FIG. 8). Although specific embodiments are described herein, it will be appreciated that the stacked encoder-decoder network can include any suitable structure configured to identify a pose and/or body region of a patient 17.

In some embodiments, a temporal information module 160 is configured to consider multiple frames simultaneously during patient pose and/or body region estimation. A temporal information module 160a can be configured to process each frame captured by an imaging device 70 to obtain robust estimates by aggregating information from multiple frames. For example, in some embodiments, each frame may be individually analyzed by a spatial information module 158, such as the spatial information module 158a discussed above, and aggregated by a temporal information module 160 to generate a single pose and/or body region estimate. The temporal information module 160 can be configured to generate a probability of each possible pose for each frame and generate a statistical value, such as a trimmed mean or median, from multiple frames to generate a final estimate for a patient pose.

In some embodiments, temporal information (e.g., multiple frames) can be aggregated for body region boundary estimate using a smoothing method (e.g., a Kalman filter) on the sequence prediction over time. Alternatively and/or additionally, in some embodiments, a recurrent neural network (RNN) 160a is configured to capture temporal information. In some embodiments, the RNN 160a is integrated into the stacked encoder-decoder network 270a, as illustrated in FIG. 8. When the RNN 160a is integrated with a stacked encoder-decoder network 270a, the RNN 160a identifies temporal information simultaneously with the processing of each individual frame by the stacked encoder-decoder network 270a. In some embodiments, the RNN 160a includes a Long Short Term Memory (LSTM) network.

Figure 9:
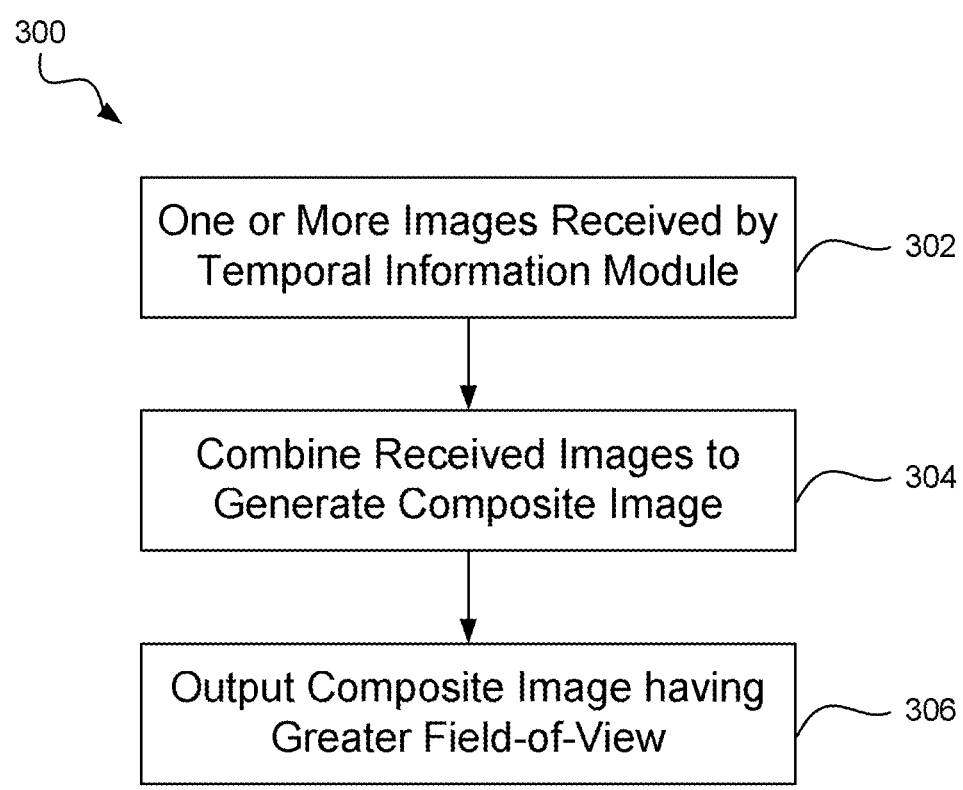
FIG. 9 illustrates a method of multi-frame analytics configured to generate a composite image from a plurality of input images, in accordance with some embodiments.
Figure 10:
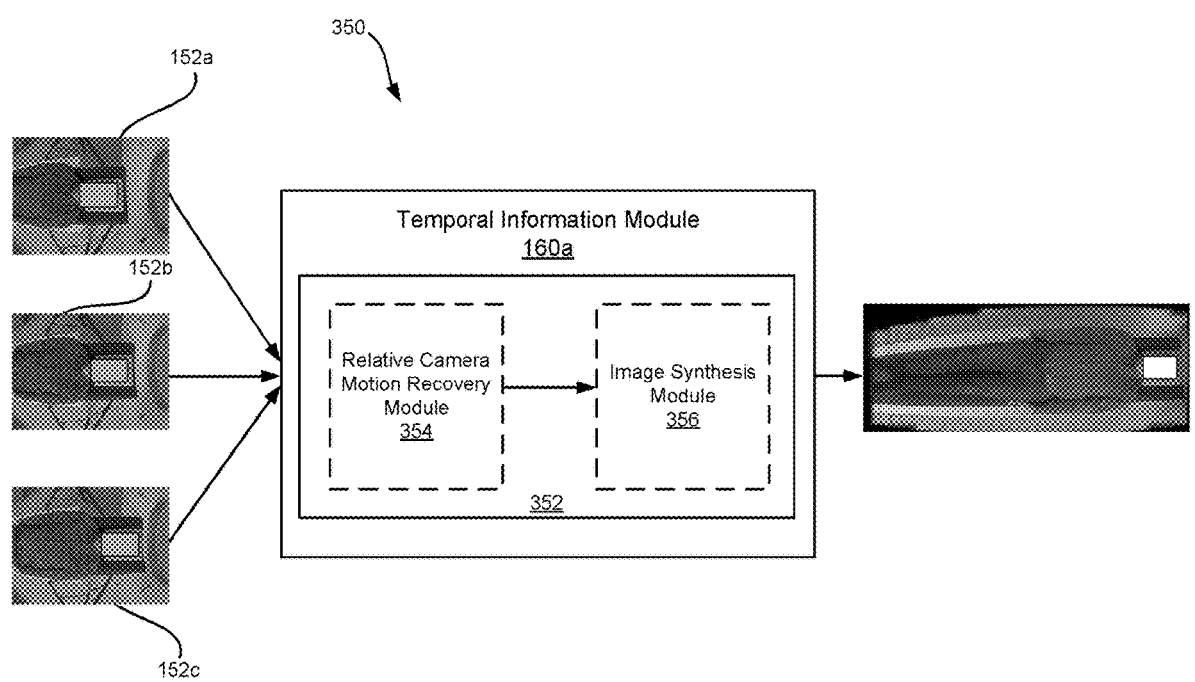
FIG. 10 illustrates a process flow of a temporal information module configured to implement the method illustrated in FIG. 9, in accordance with some embodiments.

FIG. 9 illustrates a method 300 of multi-frame analytics configured to generate a composite image from a plurality of input images, in accordance with some embodiments. FIG. 10 illustrates a process flow 350 of a temporal information module 160a configured to implement the method 300 illustrated in FIG. 9, in accordance with some embodiments. At step 302, a plurality of images 152a-152c is received by the temporal information module 160a. The temporal information module 160a includes a multi-frame analytics module 352. Each of the images 152a-152c have a limited field-of-view with respect to a patient 17 positioned on a moveable bed 18. For example, with reference again to FIG. 1, in some embodiments, an imaging device 70, such as a camera, coupled to an outer surface of a gantry 16 has a limited field of view 80 that includes only a portion of a patient 17. As the moveable bed 18 advances in a scan direction 82, the portion of the patient 17 contained within the field-of-view 80 changes. In some embodiments, the multi-frame analytics module 352 is configured to generate a composite image having a field-of-view greater than the field-of-view 80 of the imaging device 70.

At step 304, the multi-frame analytics module 352 combines two or more of the received images 152a-152c to generate a composite image 360. For example, in some embodiments, the multi-frame analytics module 352 is configured to combine two or more discrete images 152a-152c containing a portion of the patient 17 to generate a single composite image 360 having a greater field-of-view than any of the individual discrete images 152a-152c. In some embodiments, the multi-frame analytics module 352 is configured to utilize structure from motion (SFM) techniques to estimate the patient bed 18 motion and/or a depth map to generate a 3D surface of a patient 17 from the received images 152a-152c. Multiple generated 3D surfaces are combined to generate a single 3D surface image of the patient 17. In some embodiments, the multi-frame analytics module 352 is configured to implement a simultaneous localization and mapping (SLAM) technique, as discussed in greater detail below. In some embodiments, the generated composite image 360 is provided to the spatial information module 158 for determining pose and/or body region boundaries.

In some embodiments, the multi-frame analytics module 352 is configured to extend a field-of-view of the imaging device 70 by combining multiple frames from a continuous image stream (e.g., video) and/or discrete image stream obtained from the imaging device 70. For example, in some embodiments, a multi-frame analytics module 352 implements a two-step process including a relative motion recovery module 354 and an image synthesis module 356. In some embodiments, the relative motion can be inferred from the patient bed reading if it's synchronized with the image acquisition. In some embodiments, and as discussed in greater detail below, a simultaneous localization and mapping (SLAM) technique can be used for relative motion recovery and a back-projection geometric estimation can be used for image synthesis, although it will be appreciated that any suitable techniques can be used for relative motion recovery and/or image synthesis.

In some embodiments, a relative motion recovery module 354 is configured to implement one or more structure from motion (SFM) methods, SLAM methods, and/or any other suitable motion recovery methods. For example, in embodiments including two or more imaging devices 70, an SFM method applies frame matching for all possible pairs of video frames obtained by imaging devices 70 and processed by the temporal information module 160a. The SFM method is capable of handling unordered and heterogeneous data (e.g., images captured by different cameras under various environmental conditions).

In some embodiments including a single imaging device 70, the relative motion recovery module 354 includes a SLAM implementations. The temporal information module 160a is configured to track information across consecutive frames, such as frames provided by a continuous imaging device 70. In some embodiments, the SLAM method implements one or more statistical techniques to approximate a location of the patient 17 and approximate a map of the medical imaging environment. For example, the SLAM method may implement one or more of a Kalman filter, particle filter (e.g., Monte Carlo filter), scan matching, bundle adjustment and/or any other suitable technique. In some embodiments, the SLAM module is configured to generate a point map 360 (see FIG. 11).

In specific embodiments, the SLAM method can be limited by one or more imposed parameters. For example, in some embodiments, the imposed parameters can include a limitation on movement of the patient bed 18 to a predetermined range of movement (e.g., one or more degrees of freedom), such as two-degree of movement range including translation in height and/or longitudinal movement into/out of a gantry 16. As another example, in some embodiments, the imposed parameters can include a limitation of a static background such that background regions can be detected via frame differences accumulated from first view frames of the video and the assumption that the patient 17 is moving with the patient bed 18 towards the gantry 16.

In some embodiments, the relative motion recovery module 354 is configured output one or more key frames and an accompanying point map 360. For example, in some embodiments, the relative motion recovery module 354 is configured to output a point map and corresponding frame at a fixed interval and/or based on an estimated movement (e.g., output a frame after a patient 17 has moved a predetermined distance). The one or more key frames are configured to provide good spatial coverage of a patient 17 based on the provided frames from the imaging device 70. In some embodiments, key frames are selected such that overlap between nearby key frames allows geometry estimation of background and/or foreground elements by the image synthesis module 306, as discussed in greater detail below.

Figure 11:
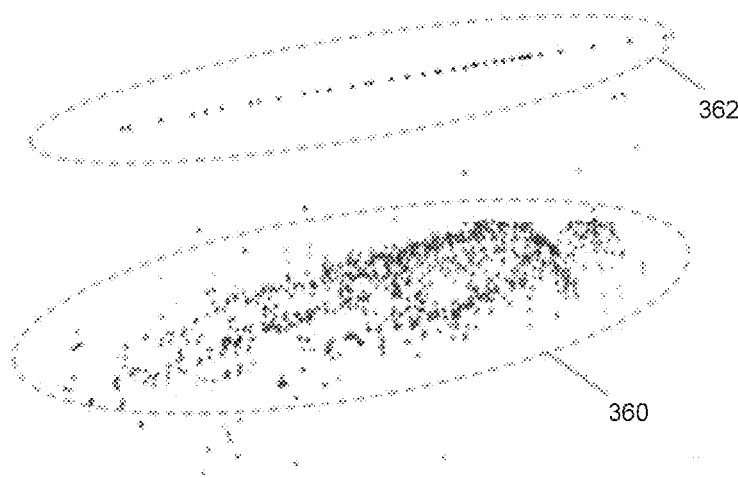
FIG. 11 illustrates a point map 360 relative to a motion track of a patient during movement of a patient bed, in accordance with some embodiments.

In some embodiments, the point map 360 includes a plurality of points (such as grid points) corresponding to detected geometry of the patient 17. For example, as shown in FIG. 11, a point map 360 can be generated relative to a motion track 362 of the patient 17 during movement of the patient bed 18. The point map 360 includes a plurality of points each corresponding to a portion of the patient 17 detected by the relative motion recovery module 354.

In some embodiments, the relative motion recovery module 354 provides a point cloud 360 (such as a sparse point cloud) for one or more key frames to the image synthesis module 356. The image synthesis module 356 is configured to estimate a patient's 3D body geometry for each received frame and corresponding point cloud. In some embodiments, the image synthesis module 356 is configured to generate a synthesized image from the input frames (i.e., key frames). The image synthesis module 356 can implement any suitable image synthesis methods, such as a depth map fusion method based on multi-view stereo matching and/or an image-based rendering method based on coarse depth estimation.

Figure 12:
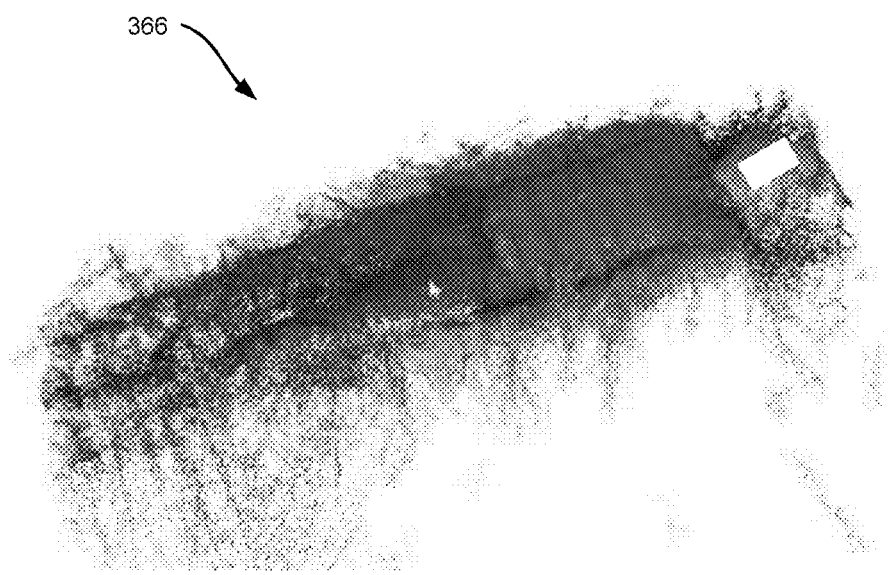
FIG. 12 illustrates a densified point cloud generated from a plurality of input images, in accordance with some embodiments.
Figure 13:
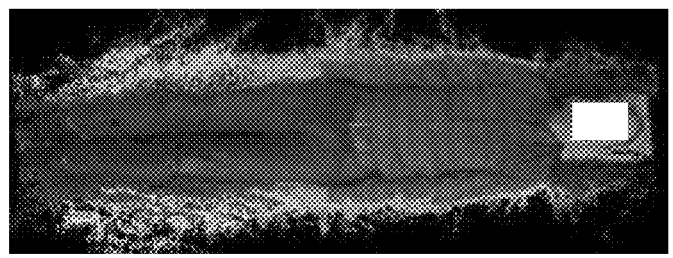
FIG. 13 illustrates a composite image generated by projecting the densified point cloud of FIG. 12 onto a virtual camera, in accordance with some embodiments.

In some embodiments, the image synthesis module 356 is implemented with includes a depth map fusion method. The depth map fusion method is configured to estimate aggregate an extended dense map from the depth map estimated for each frame for each received frame by using a one or more multi-view stereo processes. For example, in some embodiments, a multi-view stereo process uses one or more additional frames having an overlapping number of points in a point cloud 360 to estimate a dense map for each individual frame. The individual depth maps for each frame are merged together as a densified point cloud 366, illustrates in FIG. 12. The densified point cloud is projected onto a virtual camera to generate a synthesize image 370 having an extended field-of-view of the patient 17, as illustrated in FIG. 13. The synthesized image 370 of FIG. 13 has an extended field-of-view as compared to any of the individual images obtained by the imaging device 70.

Figure 14:
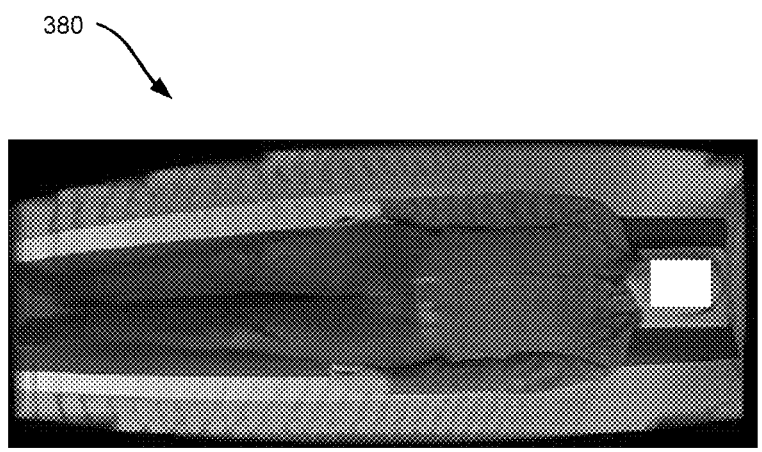
FIG. 14 illustrates a synthesized image generated using an image-based rendering method configured to apply image-based rendering with coarse geometry fitting, in accordance with some embodiments.

In some embodiments, the image synthesis module 356 includes an image-based rendering method configured to apply image-based rendering with coarse geometry fitting. In some embodiments, the image-based rendering is configured to apply coarse geometry as a proxy to project input images via the proxy (e.g., the coarse geometry) onto a virtual camera with an extended field-of-view by using image-based rendering. In some embodiments, the coarse geometry is derived from the point cloud 360 generated by the relative motion recovery module 354. FIG. 14 illustrates one embodiment of a synthesized image 380 generated using an image-based rendering method configured to apply image-based rendering with coarse geometry fitting, in accordance with some embodiments.

Referring back to FIG. 9, at step 306, the temporal information module 160 is configured to output the composite image 370, 380. In some embodiments, the temporal information module 160 is configured to provide a composite image 370, 380 to the spatial information module 158 for use in pose and/or body region estimation. For example, in some embodiments, the spatial information module 158 is configured to provide the composite image 370, 380 to one or more of the networks discussed above, such as, for example, the fully convolutional neural network 252a. The spatial information module 158 may be configured to output a pose and/or body region estimate from the provided composite image 370, 380 and/or provide additional information (such as an updated point cloud) to the temporal information module 160 for additional processing.

In some embodiments, the neural networks included in the spatial information module 158 and/or the temporal information module 160 can be trained prior to initiating a patient pose and/or body region determination and/or can be selected from pre-generated and/or pre-trained neural networks. For example, in some embodiments, a system, such as computer system 30 illustrated in FIG. 1, receives a training data set. The training data set contains a plurality of training images including at least a portion of a patient and associated data identifying information related to the training image, such as the pose of the patient contained within the image, the body region(s) contained within the image, references to a composite image generated at least partially on the training image, and/or any other suitable information. In some embodiments, the system 30 receives a plurality of training data sets each containing a plurality of training images with associated data. For example, the system 30 can receive a first training data set containing only a first pose and/or body region, a second training data set containing only a second pose and/or body region, a third training data set containing only a third pose and/or body region, etc. The training data set(s) can be received from a single source and/or can be received from multiple sources. In other embodiments, the system 30 is configured to load one or more pre-generated neural networks from a repository, such as memory and/or a network-connected storage device.

In some embodiments, the system 30 is configured to generate a neural network using the training data set, such as, for example, an FCNN network 252a, a RNN 160a, a multi-view stereo network, etc. Each neural network can be generated by providing each of the training images in the training data set to a learning network, such as an image-to-image learning network, a deep reinforcement learning network, a residual network, a densely connected convolution network, and/or any other suitable learning network. The learning network reviews each of the training images and attempts to identify one or more parameters, such as the patient pose, body region, etc.

In some embodiments, the learning network is a supervised learning network. A supervised learning networks receives the training data set and attempts to identify a neural network mapping (e.g., a neural network topography) implied by the training data set and that best maps a set of inputs (i.e., training images) to a correct output. For example, a supervised learning network provided with a training data set containing various patient poses and/or body regions generates a neural network that best maps each image to one or more pose and/or body region categories. A cost function is related to a mismatch between the selected mapping and the training data set. The cost function can include any suitable cost function, such as a mean-squared error function or categorical cross entropy loss function. In some embodiments, the learning network uses a backpropagation algorithm to calculate an error contribution of each neuron (e.g., node) in the neural network during training. The cost function is configured to identify the best neural network topography based on the training data set.

Figure 15:
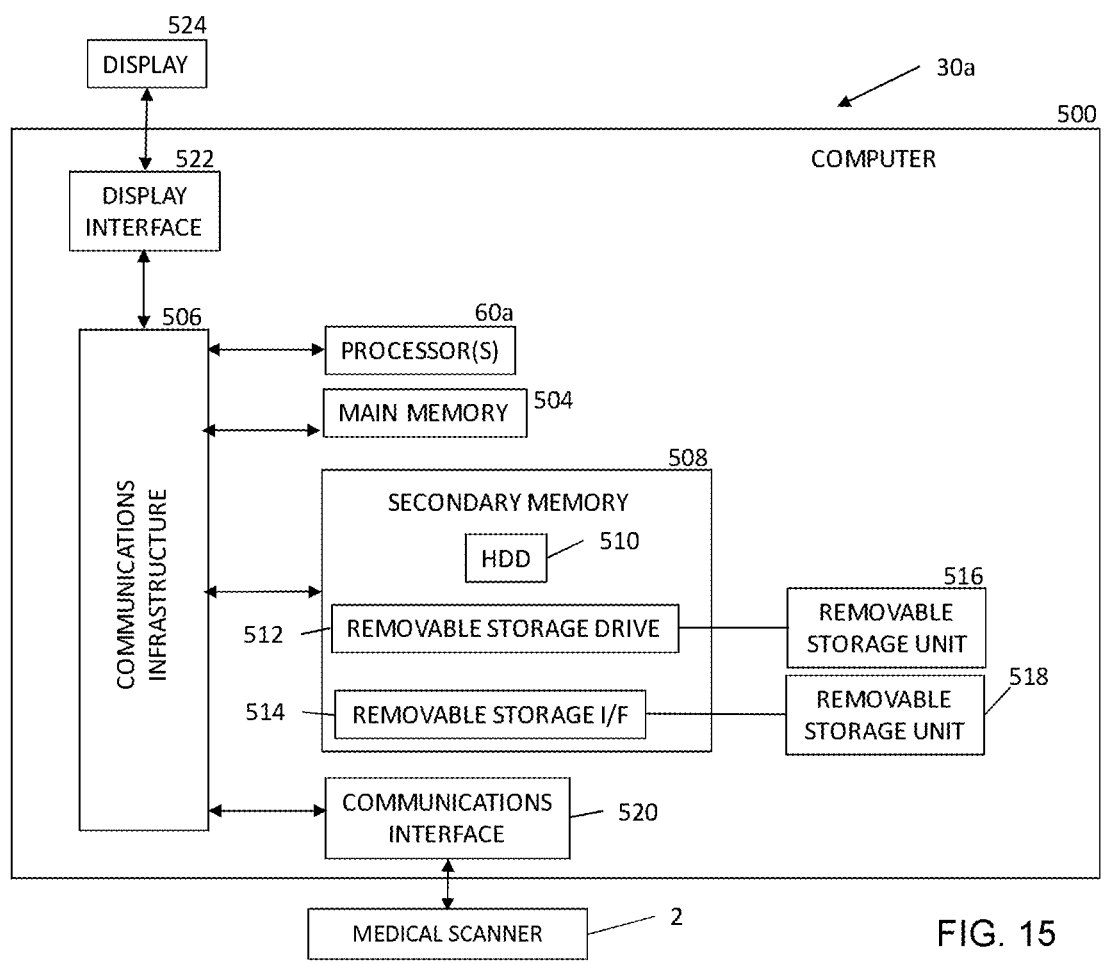
FIG. 15 illustrates a block diagram of a system for generating a medical image, in accordance with some embodiments.

FIG. 15 is a block diagram of a system 500 for generating a medical image. The system 500 includes the medical imaging system 2 and a computer system 30a. The computer system 30a can be used in some embodiments, e.g., for implementing the system 30 controlling the medical imaging system 2. Computer system 30a may include one or more processors 60a. Each processor 60a is connected to a communication infrastructure 506 (e.g., a communications bus, cross-over bar, or network). The processor 60a can be implemented as a central processing unit, an embedded processor or microcontroller, an application-specific integrated circuit (ASIC), and/or any other circuit configured to execute computer executable instructions to perform one or more steps. Processors 60a are similar to the processor 60 discussed above and similar description is not repeated herein. Computer system 30a may include a display interface 522 that forwards graphics, text, and other data from the communication infrastructure 506 (or from a frame buffer, not shown) for display on the display unit 524 to a user.

Computer system 30a may also include a main memory 504, such as a random access memory (RAM), and a secondary memory 508. The main memory 504 and/or the secondary memory 508 comprise a dynamic random access memory (DRAM). The secondary memory 508 may include, for example, a hard disk drive (HDD) 510 and/or removable storage drive 512, which may represent a solidstate memory, an optical disk drive, a flash drive, a magnetic tape drive, or the like. The removable storage drive 512 reads from and/or writes to a removable storage unit 516. Removable storage unit 516 may be an optical disk, magnetic disk, floppy disk, magnetic tape, or the like. The removable storage unit 516 may include a computer readable storage medium having tangibly stored therein (or embodied thereon) data and/or computer executable software instructions, e.g., for causing the processor(s) to perform various operations and/or one or more steps.

In alternative embodiments, secondary memory 508 may include other devices for allowing computer programs or other instructions to be loaded into computer system 30a. Secondary memory 508 may include a removable storage unit 518 and a corresponding removable storage interface 514, which may be similar to removable storage drive 512, with its own removable storage unit 516. Examples of such removable storage units include, but are not limited to, universal serial bus (USB) or flash drives, which allow software and data to be transferred from the removable storage unit 516, 518 to computer system 30a.

Computer system 30a may also include a communications interface (e.g., networking interface) 520. Communications interface 520 allows instructions and data to be transferred between computer system 30a and medical imaging system 2. Communications interface 520 also provides communications with other external devices. Examples of communications interface 520 may include a modem, Ethernet interface, wireless network interface (e.g., radio frequency, IEEE 802.11 interface, Bluetooth interface, or the like), a Personal Computer Memory Card International Association (PCMCIA) slot and card, or the like. Instructions and data transferred via communications interface 520 may be in the form of signals, which may be electronic, electromagnetic, optical, or the like that are capable of being received by communications interface 520. These signals may be provided to communications interface 520 via a communications path (e.g., channel), which may be implemented using wire, cable, fiber optics, a telephone line, a cellular link, a radio frequency (RF) link and other communication channels.

The methods and system described herein may be at least partially embodied in the form of computer-implemented processes and apparatus for practicing those processes. The disclosed methods may also be at least partially embodied in the form of tangible, non-transitory machine-readable storage media encoded with computer executable program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific connections, circuits, and algorithms for implementing the methods disclosed herein.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method for generating a medical image, comprising:
    obtaining, via a camera, at least one surface image of a patient;
    determining, from the at least one surface image, a pose of the patient using at least one spatial information module, the at least one spatial information module comprising a Dense Block Hourglass (DBHG) network;
    positioning, via a moveable bed, the patient at an imaging start position; and
    obtaining, via a medical image modality, a medical image of the patient.

2. The method of claim 1, wherein the at least one spatial information module comprises at least one of a single-frame analytics network or a multi-frame analytics network.

3. The method of claim 2, wherein the single-frame analytics network comprises a fully convolutional neural network.

4. The method of claim 1, comprising preprocessing the at least one surface image of the patient prior to determining a pose of the patient.

5. A method for generating a medical image, comprising:
    obtaining, via a camera, at least one surface image of a patient;
    determining, from the at least one surface image, a pose of the patient using at least one spatial information module, the at least one spatial information module comprising a first neural network;
    positioning, via a moveable bed, the patient at an imaging start position; and
    obtaining, via a medical image modality, a medical image of the patient
    generating a composite image from two or more of the surface images of the patient from different times, wherein the composite image is generated by a temporal information module in signal communication with the spatial information module.

6. The method of claim 5, wherein the temporal information module comprises a relative motion recovery module and an image synthesis module.

7. The method of claim 6, wherein the relative motion recovery module comprises a synchronized patient bed position reading to infer a relative motion between the patient and the camera.

8. The method of claim 6, wherein the relative motion recovery module comprises a structure from motion module, a simultaneous localization and mapping module, or a combination thereof.

9. The method of claim 6, wherein the image synthesis module comprises a depth fusion module.

10. The method of claim 9, wherein the depth fusion method aggregates the depth map for each frame estimated from multi-view stereo matching process.

11. The method of claim 9, wherein the image synthesis module synthesizes an extended field of view based on a coarse geometry fitting to the patient.

12. The method of claim 5, wherein the temporal information module comprises a recurrent neural network.

13. The method of claim 5, wherein the at least one spatial information module comprises a Dense Block Hourglass (DBHG) network.

14. A system of generating a medical image, comprising:
    an imaging modality configured to obtain a medical image of a patient;
    an imaging device configured to obtain at least one surface image of a patient; and
    a processor configured to implement a combination of a spatial information module and a temporal information module, wherein the temporal information module is configured to generate a composite image from two or more surface images of the patient from different times, wherein the processor is configured to receive the composite image of the patient and verify at least one of a patient pose or a body region, and wherein the processor is configured to execute a medical imaging procedure using the imaging modality when the patient pose or body region is verified.

15. The system of claim 14, wherein the spatial information module comprises a fully convolutional neural network.

16. The system of claim 14, wherein the spatial information module comprises a Dense Block Hourglass (DBHG) network.

17. The system of claim 14 wherein the temporal information module comprises a relative motion recovery module and an image synthesis module.

18. The system of claim 17, wherein the relative motion recovery module comprises a simultaneous localization and mapping module, a synchronized bed position module configured to infer a relative motion between the patient and the camera, or a combination thereof.

19. A non-transitory computer-readable medium encoded with computer executable instructions, the computer executable instructions, when executed by a computer in a system for reviewing image scans, cause the system for reviewing image scans to execute the steps of:

receiving at least one surface image of a patient;

determining a pose of the patient from the at least one surface image using at least one spatial information module comprising a machine-learned neural network having stacked first and second encoder-decoder pairs with the second encoder-decoder pair arranged to receive an input and output of the first encoder-decoder pair;

positioning, via a moveable bed, the patient at an imaging start position; and obtaining, via a medical image modality, a medical image of the patient.

* * * * *